United States Patent [19]

Andrews

[11] Patent Number: 4,591,442
[45] Date of Patent: May 27, 1986

[54] FLASH CHROMATOGRAPHY

[75] Inventor: Robert S. Andrews, Dana Point, Calif.

[73] Assignee: Nelson Research & Development Co., Irvine, Calif.

[21] Appl. No.: 674,600

[22] Filed: Nov. 26, 1984

[51] Int. Cl.⁴ ............................................. B01D 15/08
[52] U.S. Cl. .................................. 210/656; 210/198.2
[58] Field of Search ....................... 210/656, 659, 198.2

[56] References Cited

U.S. PATENT DOCUMENTS

| | | | |
|---|---|---|---|
| 3,935,097 | 1/1976 | Roof | 210/659 |
| 4,295,422 | 10/1981 | Still | 210/656 |
| 4,310,420 | 1/1982 | Konishi et al. | 210/659 |
| 4,379,751 | 4/1983 | Yoritomi et al. | 210/659 |

OTHER PUBLICATIONS

Application of Forced Flow Liquid Chromatography to the Determination of Iron by Seymour et al. Analytical Chemistry, vol. 43, No. 13, Nov. 1971, pp. 1734–1736.

Primary Examiner—John Adee
Attorney, Agent, or Firm—Robert J. Baran

[57] ABSTRACT

A flash chromatography apparatus and method for rapid, moderate-resolution separation of organic compounds. A solvent reservoir is pressurized with a gas, forcing solvent under pressure through tubing into and through a sorbent-packed chromatography column. More than one solvent reservoir may be provided to permit mixed-solvent elution. Alternatively, instead of pressurizing the solvent with compressed air, one or more metering pumps may be used to deliver solvent to the column. The method includes introducing a sample to be eluted into the top of a flash chromatography column, beginning elution by introducing an elution solvent under pressure into the top of the column, the elution solvent comprising a first solvent and a second solvent in a ratio from 0:1 to 1:0, modifying the elution solvent by varying the ratio of the first solvent to the second solvent, and continuing elution with the modified elution solvent.

14 Claims, 5 Drawing Figures

FLASH CHROMATOGRAPHY

BACKGROUND OF THE INVENTION

This invention relates to an apparatus and method for chromatographic separation of organic compounds, and particularly to improvements in flash chromatography.

In contrast to more conventional high-resolution absorption chromatography techniques, which may generally be used to effect purification of samples as large as 1-2 grams and require 1-3 hours, flash chromatography permits separation of samples of up to several grams in a relatively short time with moderate resolution. This now popular technique was first described by Still, et al., *J. Org. Chem.* 43, 2923 (1978).

In conventional flash chromatography, a column is filled with sorbent. After loading the chemical to be purified into the top of the sorbent, a reservoir on the top of the column is filled with solvent. This solvent is then delivered through the column, eluting the sample downward at a rate based on its affinity to the solvent and the sorbent.

Although flash chromatography has enjoyed widespread acceptance as a rapid, moderate resolution purification technique, it suffers from disadvantages in convenience, safety and reliability. For example, the amount of solvent that can be used without interruption of elution is dependent on the size of the reservoir attached to the top of the column. Beyond a certain point, increases in reservoir size can lead to a top-heavy apparatus. Moreover, if the reservoir is too small, interruption of elution to introduce additional solvent can affect the accuracy of the separation. Maintaining an inventory of various-sized reservoirs adds to equipment cost. As the length of the column increases, the danger and inconvenience of loading solvent into a reservoir at the top of the column is multiplied. Finally, access to the top of the column necessitates removal of the large solvent reservoir with attendant danger and inconvenience.

Another significant problem with conventional flash chromatography systems is the pressure control valve. In those systems, the top of the solvent reservoir on top of the column is connected directly to the pressurized air source. Pressure is regulated with a bleed valve. Air is constantly flowing into the reservoir and out of the bleed valve. One problem with this arrangement is that the head of air over the solvent is dynamic; i.e., the air is constantly exchanged. Contamination of the solvent with water, compressor oil, fitting grease, and other residual entrained substances is possible. An even more significant problem is glassware explosions. Flash chromatography reservoirs are notoriously susceptible to exploding from overpressurization, fluctuations in pressure, or fatigue. And when the reservoir is roughly in the vicinity of the chemist's head, as it is in a conventional system, the dangers of such an explosion are multiplied.

The use of multiple solvents for packing the column and/or eluting the sample is impossible in a conventional system without interrupting elution.

Accordingly, one object of the present invention is to provide an apparatus that can deliver any desired volume of solvent to a flash chromatography column.

Another object of the present invention is to provide a flash chromatography apparatus that eliminates the solvent reservoir at the top of the column.

Still another object of the present invention is to provide a flash chromatography apparatus characterized by more convenient and ready access to the top of the column.

A further object of the present invention is to provide a method for performing flash chromatography that eliminates interruptions in elution for addition of solvent.

Still another object of the present invention is to reduce the danger of solvent reservoir explosions.

Yet another object of the present invention is to provide a two-solvent capability for flash chromatography systems.

Another object of the present invention is to provide a flash chromatography apparatus wherein solvent contamination is minimized by using a relatively static head of gas to pressurize the solvent reservoir.

SUMMARY OF THE INVENTION

In furtherance of these objects, there is provided in accordance with the present invention a flash chromatography apparatus, comprising a chromatography column having a top and a bottom, with an axis extending through the top and the bottom of the column, at least one solvent reservoir located off of the axis of the column, means for pressurizing the solvent reservoir, and means for delivering pressurized solvent from the reservoir to the top of the column. When the reservoir is pressurized with a gas, the pressurized gas in the reservoir is relatively static and is not continually exchanged.

In preferred embodiments, the solvent reservoir is located below the top of the column. Flexible tubing connecting the reservoir to the column is used to deliver solvent from the reservoir to the column. A means for controlling the flow of solvent to the column is provided. This is preferably a valve in the tubing line between the reservoir and the column or a valve for pressurizing and depressurizing the reservoir with a gas. Overpressurization is avoided through use of a pressure relief valve.

This invention also encompasses a flash chromatography apparatus comprising a column having a top and a bottom, a first solvent reservoir, a second solvent reservoir, and means for selectively delivering pressurized solvent from the first reservoir and the second reservoir into the column. Pressurized solvent is provided either with a metering pump or by pressurizing the solvent reservoirs with a gas. A first metering pump may be used to deliver solvent from a first reservoir and a second metering pump may be used to deliver solvent from a second reservoir. This permits use of accurately mixed two-solvent elution systems. Alternatively, a mixing valve in the solvent lines may be used to select one solvent or the other or to deliver mixed solvent to the column.

The present invention also encompasses a kit for performing flash chromatography, comprising a chromatography column having a top and a bottom, a solvent reservoir, a fitting for introducing compressed gas into the solvent reservoir, a fitting for removing pressurized solvent from the solvent reservoir, tubing for carrying pressurized solvent from the reservoir to the column, and a fitting for introducing pressurized solvent into the column. The fittings on the solvent reservoir may be one unitary fitting.

In addition, this invention also embraces a method for performing flash chromatography, comprising the steps of introducing a sample into a chromatography column, delivering pressurized solvent through tubing from a separate solvent reservoir into the top of the column, and purifying the sample by eluting it through the column. The solvent may be pressurized by a liquid-type metering pump or by pressurizing the solvent reservoir with an inert gas or air. Again, more than one solvent reservoir may be used.

This invention also includes a method for performing flash chromatography, including the steps of introducing a sample to be eluted into the top of a flash chromatography column, beginning elution by introducing an elution solvent under pressure into the top of the column, the elution solvent comprising a first solvent and a second solvent in a ratio of from 0:1 to 1:0, modifying the elution solvent by varying the ratio of the first solvent to the second solvent, and continuing elution with the modified elution solvent. The first and second solvents may be contained, respectively, in first and second solvent reservoirs.

Unlike medium pressure liquid chromatography (MPLC), which uses pressures of about 30 to 60 psi, and requires custom-made equipment, the present invention usually operates with pressures of about 1 to 20 psi, preferably about 5 to 15 psi, using relatively inexpensive conventional glassware. In addition, the top of the column in the present invention can be easily opened to introduce sample or to replace the sorbent; sample size can generally be large; and elution is much faster than with Mplc. Moreover, in a preferred embodiment, the present invention uses only a single sorbent column.

DETAILED DESCRIPTION OF PREFERRED EMBODIMENTS

Figure 1:
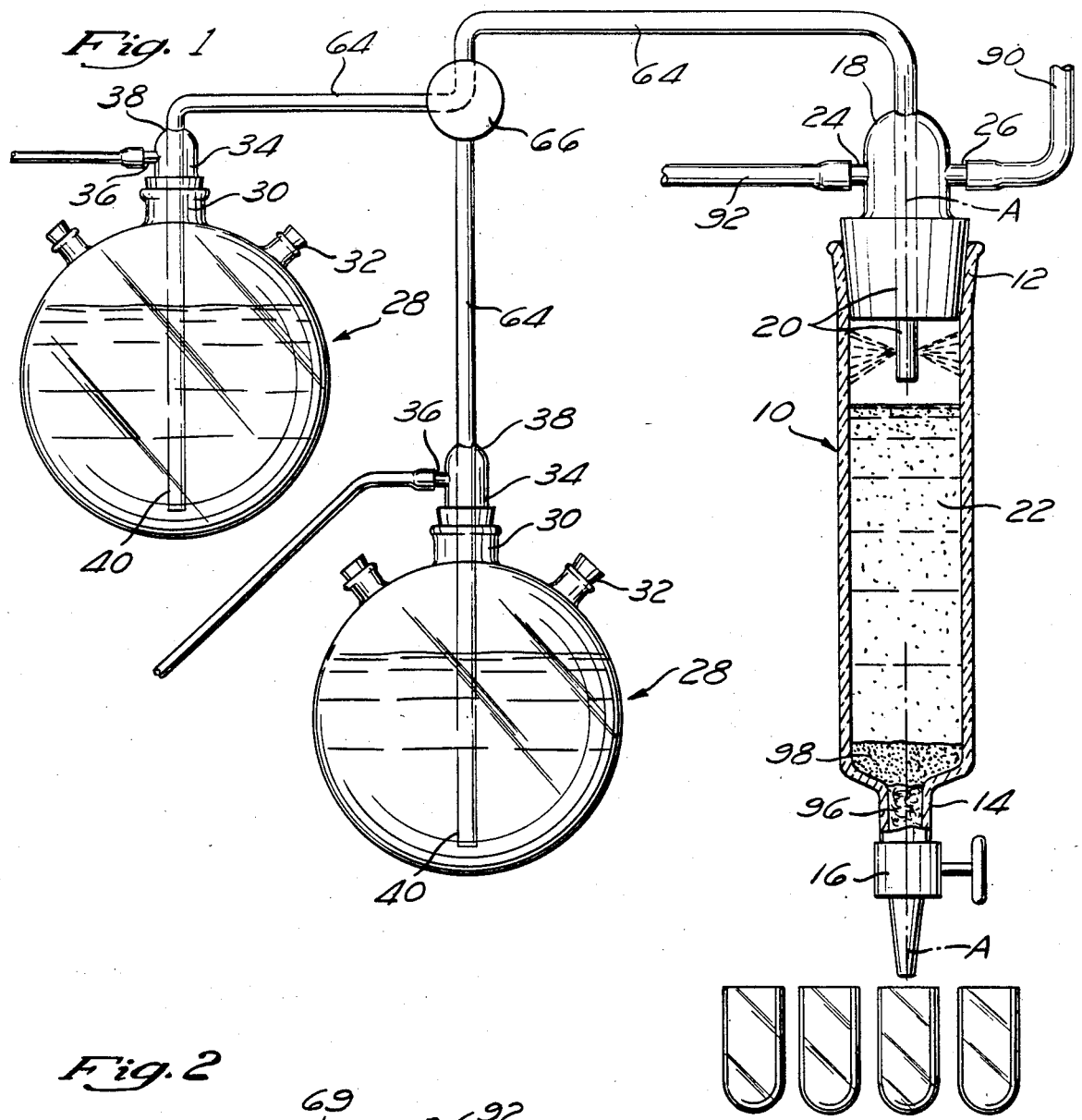
FIG. 1 is an elevation of the flash chromatography apparatus including the solvent reservoirs and column.

With reference to FIG. 1, a chromatography column 10 is provided having a top end 12 and a bottom end 14. The chromatography column 10 used in the present invention may be any elongated structure of uniform cross-section; however, a conventional elongated cylindrical column is preferred. The column 10 is typically made of glass or quartz, but may, in certain situations, advantageously be made of other suitable nonreactive materials such as polytetrafluoroethylene (Teflon ®).

The column is situated generally vertically and has a vertical axis A—A extending through the top 12 and the bottom 14.

A conventional column stopcock 16 is provided at the bottom 14 of the column 10.

A column fitting 18 is attached to the top 12 of the column 10 through which solvent is introduced. The column fitting 18 may be formed of the same material as the column 10, or any other suitable material that is nonreactive with the sample and the solvent to be used. Solvent is introduced through a solvent tube 20 extending through the column fitting. The solvent tube 20 preferably sprays the solvent radially or laterally onto the walls of the column 10 rather than directly onto the sorbent 22 with which the column is packed to avoid disruption of the sorbent 22.

The column fitting 18 advantageously has an air exhaust port 24 communicating with the interior of the column 10 through which gas may be removed from the column 10. An auxiliary port 26 may also be provided on the column fitting 18 through which a sample, a second solvent, or other fluid is introduced.

At least one, and preferably at least two separate (i.e., not directly connected to the column) solvent reservoirs 28 are situated generally adjacent to the column 10. The solvent reservoirs 28 may be made of any suitable non-contaminating material that is compatible with the solvent. As with the column 10, suitable materials include glass, quartz, polytetrafluoroethylene, or other nonreactive polymer, such as polyethylene or polyvinylidene chloride. Of course, selection of the solvent reservoir material depends on the reactivity of the solvent, and, to some extent, of the sample. In each instance, the appropriate material will be apparent to one of ordinary skill in the art.

The solvent reservoirs 28 are provided with a first opening 30, preferably at the top of the reservoirs 28. Compressed gas, such as nitrogen, argon, xenon, neon, or, where the reactivities of the solvent and sample permit, air, is introduced into the reservoir through the first opening 30. A second opening 32 may also be provided, also preferably in the top of the reservoir 28. Solvent can be added or removed through this second opening 32.

In a preferred embodiment, a reservoir fitting 34 is attached to the the first opening 30. The reservoir fitting 34 has a first port 36 for introducing gas into the top of the reservoir, and a second port 38 in fluid communication with the bottom of the reservoir 28 for removing pressurized solvent from the reservoir 28. A tube 40 extending from the second port to the vicinity of the bottom of the reservoir, or at least beneath the surface of the solvent, can be used to direct pressurized solvent to the second port 38 when compressed gas is introduced through the first port 36.

Figure 3:
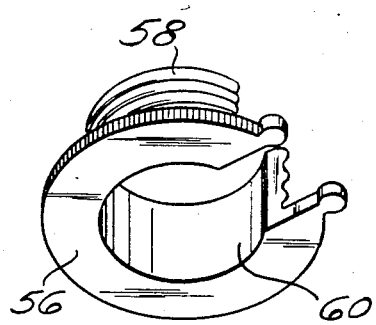
FIG. 3 is a vertical cross section of the solvent reservoir opening and fitting.

Of course, there are many alternative embodiments having the equivalent function. For example, compressed gas may be introduced into the top of the reservoir 28 through the first opening 30, and pressurized solvent may be removed from an opening (not shown) in the bottom of the reservoir 28. Alternatively, compressed gas may be introduced into the first opening 30, and pressurized solvent may be removed from the second opening 32. The reservoir fitting 34 may be attached to the reservoir 28 by using conventional pinch clamps or by any other suitable method for joining materials. However, a preferred embodiment utilizing a commercially available screw fastener is shown in FIG. 3. A conventional female 24/40 glass joint 42 is provided in a neck 44 on the first opening 30 of the solvent reservoir. The reservoir fitting 34 has a matching 24/40 male joint 46. An annular nut 48 having inside female threads 50 is placed over the male joint 46 on the reservoir fitting 34. The nut 48 has an inwardly extending annular shoulder 52 at one end thereof. An O-ring 54 is placed over the male joint 46 to retain the nut 48 on the reservoir fitting 34.

A sleeve segment 56 having matching outside male threads 58 is snapped onto the outside of the neck 44 and is screwed into the nut 48, compressing the "O" ring 54 against the shoulder 52 of the nut 48 and against the reservoir fitting 34 to hold the male and female joints 42 and 46 together. The column fitting 18 may be attached to the column 10 in the same manner.

Figure 4:
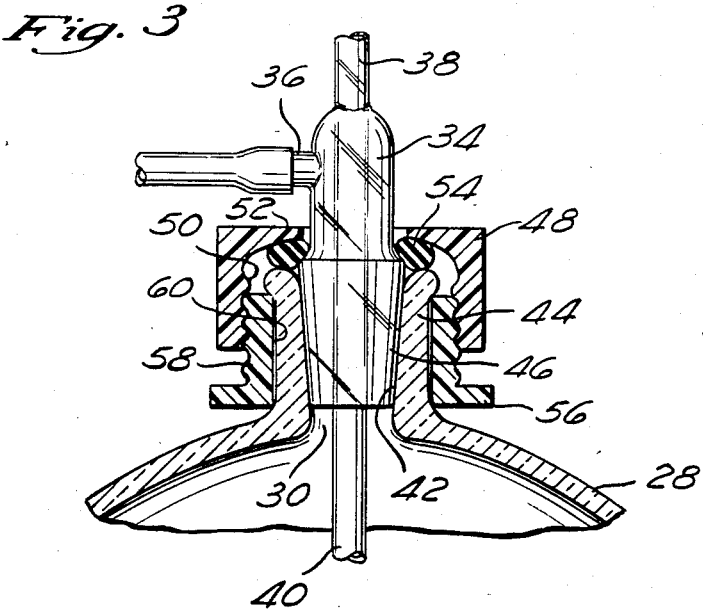
FIG. 4 is a perspective of a screw fastener used to secure glassware joints.

The sleeve segment 56 is shown more clearly in FIG. 4. It has a smooth interior portion 60 and male exterior threads 58 on a generally cylindrical body. One segment of the cylinder is missing, leaving an opening 62. The sleeve segment 56 is made of a rigid polymeric material with enough "give" that it may be snapped over the neck 44 of the reservoir 28.

The glassware used in the simplest embodiment of the present invention may all be conventional. Columns 10 of many diameters and lengths are commercially available. The solvent reservoirs 28 may be conventional round-bottom flasks having 1, 2, or 3 necks, as desired. The column and reservoir fittings 18 and 34 are commercially available from Cole Scientific Company and Ark Distribution Company. It is preferred that the reservoir, column, and fittings all have tapered ground glass fittings, e.g., standard 24/40 fittings. The screw fasteners for the glassware joints are available from Witeg Scientific Company.

Tubing 64 is provided connecting the reservoir fitting 34 to the column fitting 18 to deliver pressurized solvent from the reservoir 28 to the column 10. Any non-contaminating solvent compatible tubing, such as glass tubing, may be used; however, polytetrafluoroethylene tubing is preferred. In a preferred embodiment, at least some of the tubing 64 connecting the solvent reservoir 28 to the column 10 is flexible tubing, preferably polytetrafluoroethylene. The use of flexible tubing simplifies set up of the apparatus and facilitates free access to the top 12 of the column 10. Such access is possible by simply removing the column fitting. It is not necessary, when flexible tubing is employed, to disconnect the tubing 64 from the column fitting 18 prior to removing the fitting 18 from the column 10.

Where two solvent reservoirs 28 are provided, each may contain a different solvent. One solvent may be used for packing or cleaning the column 10, and the other for eluting the sample. In more sophisticated applications, elution may begin with one solvent and be completed with a different solvent, or a mixture of solvents may be delivered to the column 10.

A solvent valve 66 is provided between the reservoirs 28 and the column 10 to control delivery of solvent to the column 10. This valve 66 may be a two way valve for selecting between reservoirs, or a mixing valve for mixing solvents from each reservoir 28 in any desired ratio. The solvent valve 66 can also be used to interrupt flow of solvent into the column 10. This permits delivery of metered amounts of solvent to the column 10 and definite commencement and cessation of elution at a predetermined rate without the hysterisis resulting from building up and dissipating a pressure "head" on the solvent reservoir 28. The positive control of elution rate possible with this invention facilitates the use of automatic sample collectors for collecting uniform samples at regular intervals.

Figure 5:
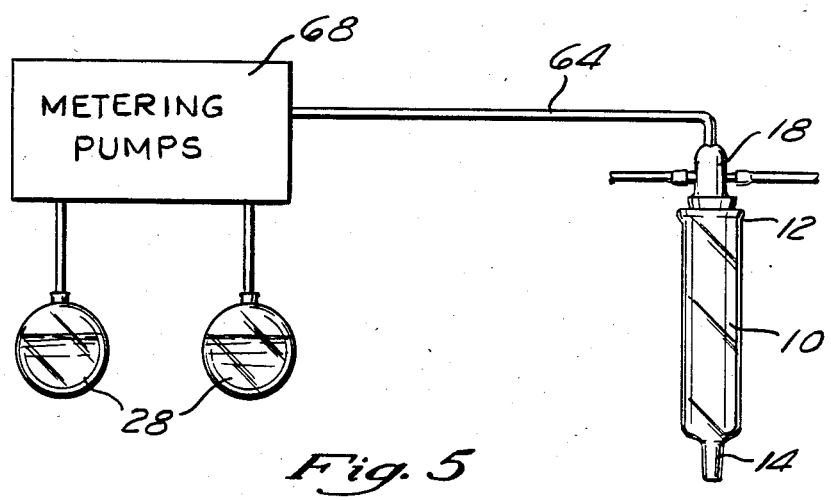
FIG. 5 is a schematic view of a modified flash chromatography system.

In another embodiment of the present invention, illustrated in FIG. 5, a conventional metering pump 68 is used to deliver pressurized solvent from the reservoirs 28 to the column 10 at any desired pressure. A second metering pump may be utilized in conjunction with the first metering pump 68 to effect precisely controlled delivery of mixed solvents to the column 10. The metering pump may be a piston pump, a peristaltic pump, or other conventional pump. The use of metering pumps 68 for solvent delivery is a significant step toward automated process control for flash chromatography.

One of the important advantages provided by this improved flash chromatography apparatus is the flexibility it permits in location and size of the solvent reservoirs 28. It is neither necessary nor desirable to attach the solvent reservoirs 28 directly to the top of the column 10. Instead, the separate reservoir 28 may be located beside the column 10 or beneath the column 10, and need not be coaxial with the column 10. Perhaps the most convenient setup is to locate the reservoir 28 on the lab bench beside the column 10. By providing the reservoir 28 in a convenient location below the top of the column 10, the heretofore awkward and dangerous procedures involving removal of the solvent reservoir from the top of the column, replacement of the solvent reservoir on the column, and filling the reservoir on the top of the column with solvent are eliminated.

The present invention also provides significant advantages in process control. Just as the solvent reservoirs 28 may be located at bench top level, so, too, the controls for pressurizing and evacuating the system and for bleeding air from the column 10 can all be conveniently and centrally located.

Figure 2:
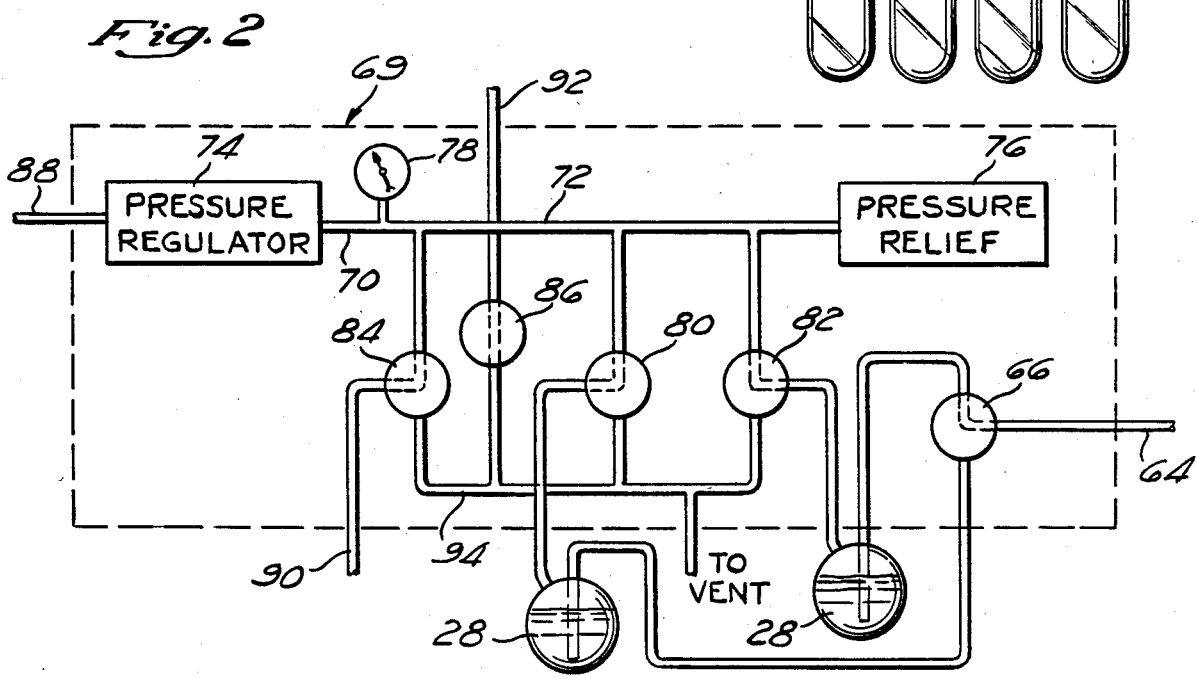
FIG. 2 is a schematic of the fluid control panel for the chromatography apparatus.

One preferred configuration for a process control station 69 is shown in FIG. 2. Pressurized gas is delivered via gas tubing 70 to a manifold 72. (In a simple embodiment, the manifold comprises a "T" connector or connectors.) To avoid overpressurization, a conventional adjustable or fixed pressure regulator 74 is located upstream from the manifold. Regardless of whether a pressure regulator 74 is provided, it is highly desirable to provide a pressure relief valve 76 in the system, preferably connected to the manifold 72. A pressure gauge 78 attached to the manifold indicates gas pressure.

The manifold 72 is connected to the first port 36 on the reservoir fitting 34 through a first reservoir pressure valve 80. The reservoir pressure valve 80 is preferably a three-way stopcock. The reservoir pressure valve 80 can connect the reservoir to the source of pressurized gas, or can be used to vent pressure in the reservoir 28 either to ambient or to a vacuum source. A second reservoir pressure valve 82 is provided when more than one reservoir 28 is used.

Also connected to the manifold is an auxiliary pressure valve 84. This valve is connected to a port on the column fitting 18. This port may be the auxiliary port 26, or another port (not shown). The auxiliary pressure valve 84 may advantageously be a three-way stopcock, and can be used to connect the column 10 directly to pressurized gas, to a vacuum source, or to ambient.

A column bleed control valve 86 is also provided. This valve connects the air exhaust port 24 to ambient or vacuum. It is desirable to restrict the vent of the auxiliary pressure valve 84 and the column bleed valve 86 to prevent rapid depressurization of the column 10 and attendant disruption of the sorbent 22.

A gas inlet line 88 carries pressurized gas into the control station 69 through the regulator 74. Pressurized gas is delivered directly to the column through the auxiliary pressure valve via a gas outlet line 90 to the auxiliary port 26 of the column fitting 18. Air is evacuated from the column 10 through the air exhaust port 24 and is carried to the column bleed valve 86 via bleed line 92. Pressurized solvent is carried to the column via solvent line 64. The vent line 94 vents the first and second reservoir pressure valves 80, 82, the auxiliary pressure valve 84, and the column bleed valve 86 to ambient or vacuum.

The reservoir pressure valves 80, 82, the auxiliary pressure valve 84, the solvent valve 66, and the column bleed valve 86 are all preferably formed of noncontaminating, nonreactive material. Tetrafluorethylene (Teflon ®) is particularly preferred. These valves are connected to the manifold 72, the reservoirs 28, and the column by suitable tubing 64, 70, such as polyethylene or tetrafluorethylene tubing. While tubing routing is a matter of choice, it is preferred that rigid tubing be employed for portions of the line that are not moved when removing the column fitting 18 and the reservoir fitting 34. The remainder of the tubing 64, 70 is preferably flexible tubing.

The column is packed and prepared for use generally as described in Still, et al., *J. Org. Chem.* 43, 2923 (1978), which is hereby incorporated by reference. In particular, a glass wool plug 96 is placed in the tube connecting the column stopcock to the column. A 3 mm layer of 50-100 mesh sand 98 is placed on plug 96 in bottom of the column 10. The column 10 is then filled with an appropriate sorbent 22. Although sorbent choice depends on the particular separation to be attempted, a general purpose sorbent 22 suitable for most organic separation is 200-425 mesh silica gel, grade 60. The sorbent 22 is then optionally topped with another thin layer of sand (not shown).

The column 10 is prepared by opening the column stopcock 16 and pressurizing the reservoir 28 by actuating the reservoir pressure valve. Pressurized solvent flowing into the column through the solvent valve 66 forces the air out of the sorbent 22 through the column stopcock 16.

The column 10 is then depressurized and the sample (preferably neat) is introduced into the top of the column 10. This can be done either by directing the sample through the auxiliary port 26, or by pipette after removing the column fitting. The sample should be evenly distributed over the top of the sorbent 22. The amount of sample introduced depends, of course, on the sorbent and solvents used and on the column size. For example, where $\Delta R_f \geq 0.10$, a 100 ml column packed with silica gel with a 19 mm ID can easily handle a 350 mg sample; a 250 ml, 30 mm ID column can purify a sample of up to 600 mg; while a 650 ml, 37 mm ID column can, in a single pass, effect separation of samples up to 1 g. Where $\Delta R_f$ values are higher so lower resolution is acceptable, samples up to 40 g can be used.

After loading the sample into the column 10, a small amount of solvent is introduced through the solvent control valve 66 to carry the sample into the sorbent 22. The auxiliary pressure valve 84 is then used to direct pressurized gas into the column 10 and drive the sample and solvent into the sorbent 22. Once the sample is in the sorbent 22, a steady stream of pressurized solvent is delivered to elute the sample. The elution rate is best controlled by controlling the solvent reservoir pressure. In general, the pressure is about 1 to 20 psi, and preferably about 5 to 15 psi. Preferred elution rates for rapid, medium resolution separations are about 30-70 mm/min. and preferably about 50 mm/min.

The $R_f$ values of the target compound and of the impurities in the sample depend on the affinities of those compounds to the solvent and to the sorbent. Of course, it is not practical to change the sorbent during the elution. However, with the present invention, the solvent composition may be readily varied during elution.

For example, a series of TLC plates of a sample may reveal some relatively nonpolar impurities having a relatively high $R_f$ in low polarity solvent, whereas the $R_f$ of the more polar target compounds is a lower value in the same solvent. In that case, the high $R_f$ nonpolar impurities can be rapidly removed by commencing elution with a relatively nonpolar solvent mixture, such as 20% diethylether and 80% petroleum ether. The target compound, meanwhile, would be moving very slowly and would be in the top part of the column, perhaps tightly grouped with other polar impurities. To complete the elution, a higher-polarity elution solvent, such as pure diethylether, can then be used to move the target compound more rapidly through the column and to increase the $\Delta R_f$ between the target compound and the remaining impurities.

EXAMPLE 1

Purification of Thiacyclohexan-4-one

A column (760 mm×25 mm) was packed with 230-400 mesh Silica Gel 60. The air was forced out the sorbent with 85% Hexane/15% Ethyl Acetate. A 13.5 gm sample of the impure Thiacyclohexan-4-one, dissolved in 7.5 ml Ethyl Acetate and 42.5 ml Hexane, was then introduced into the top of the column. This was eluted with 85% Hexane/15% Ethyl Acetate at a rate of 10 ml/min. Compressed air (10 lbs/in.$^2$) was used to pressurize the solvent reservoir. One hundred fractions of 25 ml each were collected, and the appropriate fractions (#10-40) as determined by thin layer chromatography were pooled. Concentration of this solution gave 11.82 gm (52%) of a white solid, m.p. 62°-64° C.

What is claimed is:

1. A flash chromatography apparatus, comprising:
   a chromatography column having a top and a bottom, with an axis extending through the top and the bottom of the column;
   a solvent reservoir located off of the axis of the column;
   means for pressurizing the solvent reservoir with air;
   means for delivering pressurized solvent from the reservoir to the top of the column; and
   means for preventing over pressurization of said solvent reservoir comprising an overpressure relief valve system between said solvent reservoir and said means for pressurizing the solvent reservoir.

2. The apparatus of claim 1, wherein the solvent reservoir is located below the top of the column.

3. The apparatus of claim 2, further comprising flexible tubing connecting the reservoir to the column for delivering pressurized solvent from the reservoir to the column.

4. The apparatus of claim 2, further comprising means for controlling the flow of solvent from the reservoir to the column.

5. The apparatus of claim 4, wherein the flow controlling means includes a valve for pressurizing and depressurizing the reservoir.

6. The apparatus of claim 4, wherein the flow controlling means includes the valve in the solvent flow path between the reservoir and a column.

7. The apparatus of claim 1 wherein said means for pressurizing said solvent reservoir with air provides a pressure of from about 1 to 20 psi.

8. A flash chromatography apparatus, comprising:
   a column having a top and a bottom;
   a first solvent reservoir;

a second solvent reservoir;

means for pressurizing the first and second solvent reservoir with air;

means for selectively delivering pressurized solvent from the first solvent reservoir and the second solvent reservoir into the column; and means for preventing overpressurization of the first and second solvent reservoirs comprising an overpressure valve system between said means for pressurizing the first and second solvent reservoir with air and the first solvent reservoir.

9. The apparatus of claim 8, further comprising:

means for removing pressurized solvent from the first solvent reservoir and the second solvent reservoir;

a tubing line connecting the first solvent reservoir and the second solvent reservoir to the column for delivering pressurized solvent to the column; and a valve in the tubing line for controlling the delivery of pressurized solvent to the column.

10. The apparatus of claim 9, wherein the valve in the tubing line can selectively connect either the first reservoir or the second reservoir to the column.

11. The apparatus of claim 10, wherein the valve in the tubing line further permits delivery of a mixture of solvents from the first solvent reservoir and the second solvent reservoir to the column.

12. The apparatus of claim 8 wherein said means for pressurizing the first and second reservoir with air provides a pressure of from about 1 to 20 psi.

13. In a method for performing flash chromatography, comprising the steps of:

introducing a sample into a chromatography column;

delivering compressed air-pressurized solvent at a pressure of from about 1 psi to about 20 psi through tubing from a separate solvent reservoir into the top of the column; and purifying the sample by eluting it through the column with the pressurized solvent, the improvement comprising minimizing solvent contamination by providing a relatively static head of air to pressurize the solvent reservoir.

14. The method of claim 13, further comprising the step of delivering compressed air-pressurized solvent through tubing from a second separate solvent reservoir into the top of the column.

* * * * *